United States Patent
Christian et al.

(10) Patent No.: US 10,449,005 B2
(45) Date of Patent: Oct. 22, 2019

(54) ADAPTOR FOR RECEIVING A NAVIGATED STRUCTURE WHICH IS AT LEAST A PART OF A MEDICAL OBJECT AND METHOD OF REGISTERING A NAVIGATED STRUCTURE USING THE ADAPTOR

(71) Applicant: Brainlab AG, Munich (DE)

(72) Inventors: Georg Christian, Neufahrn (DE); Thomas Feilkas, Kirchseeon (DE)

(73) Assignee: Brainlab AG, Munich (DE)

( * ) Notice: Subject to any disclaimer, the term of this patent is extended or adjusted under 35 U.S.C. 154(b) by 1042 days.

(21) Appl. No.: 14/774,760

(22) PCT Filed: Mar. 20, 2013

(86) PCT No.: PCT/EP2013/055746
§ 371 (c)(1),
(2) Date: Sep. 11, 2015

(87) PCT Pub. No.: WO2014/146701
PCT Pub. Date: Sep. 25, 2014

(65) Prior Publication Data
US 2016/0030129 A1 Feb. 4, 2016

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/39* (2016.02); *A61B 2017/00486* (2013.01);
(Continued)

(58) Field of Classification Search
CPC .......... A61B 34/20; A61B 2017/00486; A61B 2017/00876; A61B 2034/207; A61B 2090/3983; A61B 90/39
See application file for complete search history.

(56) References Cited

U.S. PATENT DOCUMENTS

| 5,987,960 A | 11/1999 | Messner et al. |
| 7,043,961 B2 | 5/2006 | Pandey et al. |

(Continued)

FOREIGN PATENT DOCUMENTS

| DE | 103 53 316 | 6/2005 |
| DE | 50 2005 003 316 | 4/2008 |

(Continued)

OTHER PUBLICATIONS

International Search Report and Written Opinion for International Application No. PCT/EP2013/055746 dated Jan. 8, 2014 (4 pages).

*Primary Examiner* — Michael T Rozanski
(74) *Attorney, Agent, or Firm* — Tucker Ellis LLP

(57) ABSTRACT

An adaptor for receiving a navigated structure, wherein the navigated structure is at least a part of a medical object which carries an object reference, and for being connected to a registration tool in order to register the navigated structure in a medical navigation system, the adaptor comprising at least two adaptor parts which, in an assembled state, form a structure receiving recess in the shape of the navigated structure and an adaptor coupling part for connecting the adaptor to the registration tool in a predetermined relative position.

12 Claims, 3 Drawing Sheets

Figure 1:
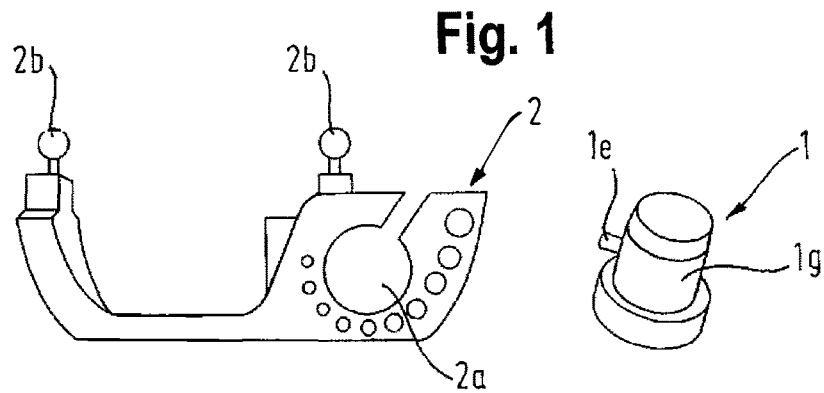

(51) Int. Cl.
*A61B 9/00* (2006.01)
*A61B 17/00* (2006.01)

(52) U.S. Cl.
CPC ............ *A61B 2017/00876* (2013.01); *A61B 2034/207* (2016.02); *A61B 2090/3983* (2016.02)

(56) References Cited

U.S. PATENT DOCUMENTS

| | | |
|---|---|---|
| 7,771,436 B2 | 8/2010 | Moctezuma De La Barrera et al. |
| 7,809,184 B2 | 10/2010 | Neubauer et al. |
| 2003/0040879 A1 | 2/2003 | Jutras et al. |
| 2005/0096536 A1 | 5/2005 | Peterson |
| 2005/0203528 A1 | 9/2005 | Couture et al. |
| 2015/0182293 A1* | 7/2015 | Yang ................ A61B 5/064 600/424 |

FOREIGN PATENT DOCUMENTS

| | | |
|---|---|---|
| EP | 1719472 | 11/2006 |
| EP | 1369090 | 12/2010 |
| EP | 1935362 | 4/2011 |

* cited by examiner

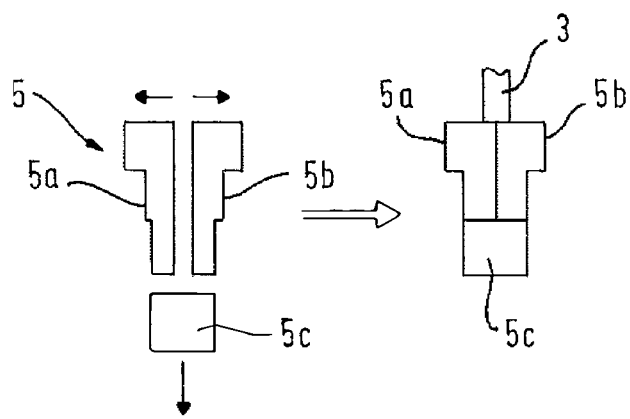
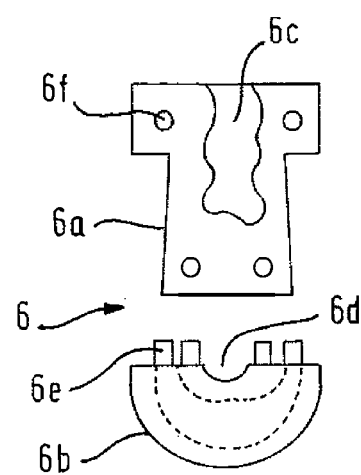
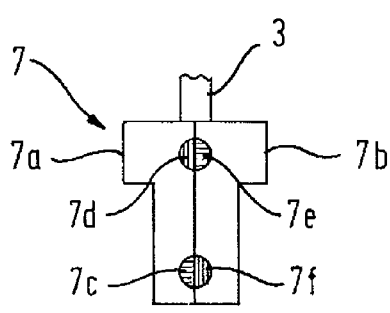
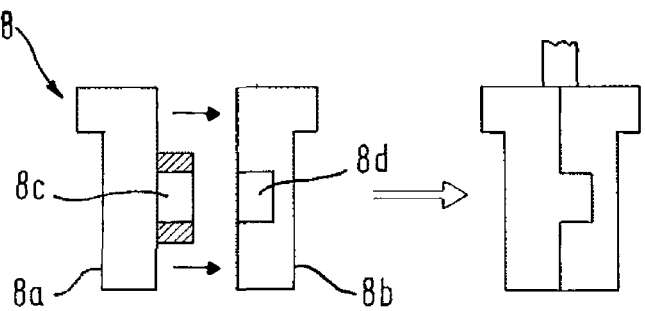
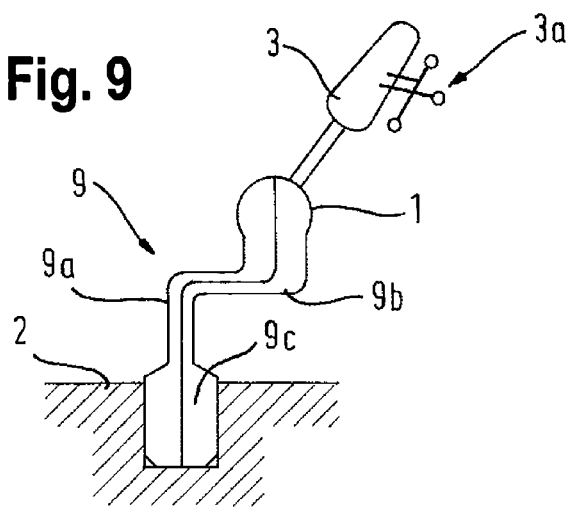

ADAPTOR FOR RECEIVING A NAVIGATED STRUCTURE WHICH IS AT LEAST A PART OF A MEDICAL OBJECT AND METHOD OF REGISTERING A NAVIGATED STRUCTURE USING THE ADAPTOR

RELATED APPLICATION DATA

This application is a national phase application of International Application No. PCT/EP2013/055746 filed Mar. 20, 2013 and published in the English language.

The present invention relates to an adaptor for receiving a navigated structure, wherein the navigated structure is at least part of a medical object which carries an object reference, and for being connected to a registration tool in order to register the navigated structure in a medical navigation system. It also relates to a method of registering the navigated structure using the adaptor.

Image-guided surgery is proving increasingly popular in improving the precision and success of surgeries. Objects to be navigated are provided with references such as marker devices which can be tracked using a medical navigation system, wherein "tracking" means determining the position of the object. The object must be registered to its reference in order for the medical navigation system to know the positional relationship between the object and its reference. It is often sufficient to navigate only a part of an object. The part of an object which is to be navigated is referred to as the "navigated structure" in this document. Depending on the object, the navigated structure can be the whole object or only part of the object. The navigated structure is typically located at the distal end of the medical object. The opposite end of the medical object is referred to as the proximal end.

The object is preferably a medical instrument or an implant. In the case of a medical instrument, only a part of it is typically of interest for the purpose of navigation. A scalpel, for example, consists of a handle and a blade, wherein the blade is the navigated structure of the scalpel. In another example, the navigated structure of a biopsy needle is its tip. If the object is an implant, then typically only a part of the implant's surface has to be navigated, and this part of the surface is then the navigated structure of the implant.

Medical navigation systems typically have a database of pre-calibrated instruments, comprising entries which represent the registration between a navigated structure of an object and the object reference. However, if a new instrument or implant, for example a customised implant, is to be used, then it has to be provided with a reference and registered in order to be navigated in the medical navigation system. The present invention relates to an adaptor which is used for registering a navigated structure in a medical navigation system, and to a method of registering a navigated structure using such an adaptor, according to the independent claims.

In accordance with the invention, an adaptor for receiving a navigated structure, wherein the navigated structure is at least part of a medical object which carries an object reference, and for being connected to a registration tool in order to register the navigated structure in a medical navigation system comprises at least two adaptor parts which, when assembled, form a structure-receiving recess in the shape of the navigated structure. In other words, the adaptor parts constitute a negative mould of the shape of the navigated structure. This means that the adaptor can receive the navigated structure in such a way that the relative position between the adaptor and the navigated structure is known. The adaptor also comprises an adaptor coupling part for connecting the adaptor to the registration tool in a predetermined relative position. This means that when the adaptor and the registration tool are connected, the navigated structure is in a known position relative to the registration tool. The registration tool carries a registration tool reference which is registered to a registration tool coupling part which is provided in order to be connected to the adaptor coupling part. The registration tool can thus be tracked, which means that the navigation system can determine the position of the registration tool.

Within this context, "being provided with", "carrying" or "having" a reference means that the reference is or can be fixed to an object, which in turn means that an invariable relative position between the object and the reference is or can be obtained. In this document, the terms "position", "relative position" and "positional relationship" encompass both a spatial location in up to three translational dimensions and an alignment in up to three rotational dimensions.

In accordance with the invention, a method of registering a navigated structure, wherein the navigated structure is at least part of the medical object which carries an object reference, in a medical navigation system comprises the steps of providing an adaptor as described in this document and assembling the adaptor parts with the navigated structure located within the structure-receiving recess. The method also comprises the step of connecting the adaptor coupling part to a registration tool coupling part of a registration tool comprising a registration tool reference. Once this step has been performed, the navigated structure has a known position relative to the adaptor and the adaptor has a known position relative to the registration tool. Since the registration tool is registered to its registration tool reference, this means that the medical navigation system knows the relative position between the navigated structure and the registration tool reference.

The method also comprises the steps of determining the relative reference position between the object reference and the registration tool reference and registering the navigated structure by calculating the relative position between the navigated structure and the object reference from the relative reference position, the known relative position between the registration tool reference and the registration tool coupling part and the known relative position between the adaptor coupling part and the structure-receiving recess.

Using the present invention, a navigated structure of any medical object can be registered in a medical navigation system by providing a suitable adaptor. Since the adaptor comprises at least two adaptor parts, the structure-receiving recess can be individually adapted to the shape of the navigated structure. The structure-receiving recess can in particular comprise undercuts, which would be impossible if the adaptor consisted of just one adaptor part. The navigated structure is for example clamped between the adaptor parts.

When the adaptor parts are "assembled", they have a predetermined relative position in which they constitute the structure-receiving recess. If they exhibit any other relative position, then they are not considered to be assembled.

In one embodiment, the adaptor also comprises a movement prevention member which prevents a relative movement between the navigated structure and the adaptor when the adaptor parts are assembled and the navigated structure is located in the structure-receiving recess. The movement prevention member can be constituted by at least a part of the boundary of the structure-receiving recess, i.e. at least a part of at least one adaptor part. In other words, there is a form fit or positive lock between the adaptor parts and the navigated structure. A contact between the surface of at least one adaptor part forming the structure-receiving recess and the navigated structure prevents the navigated structure from being removed from the structure-receiving recess.

In another example, the movement prevention member is a part of the adaptor which interacts with another part of the medical object which is not the navigated structure. If the medical object is for example a chisel, then the navigated structure is the cutting edge of the chisel. A constricted neck is typically arranged between the cutting edge and a handle of the chisel. The movement prevention member is then preferably a collar which interacts with the neck in order to prevent a relative movement between the medical object, and therefore the navigated structure, and the adaptor. The movement prevention member can also be a dead stop which interacts with the proximal end of the medical object.

There are several ways of obtaining the shape of the navigated structure. A first option is to obtain a 3D dataset or model which represents the shape of at least the navigated structure, wherein the 3D dataset can be the dataset used when the medical object is designed or manufactured. A second option is to measure the navigated structure, for example using stereoscopic imaging or laser scanning. The adaptor parts can for example be produced using rapid prototyping, which is particularly advantageous if only a small number of adaptors are required, as for example in the case of customised implants, or for example by batch production, which is particularly advantageous if a large number of adaptors is required, as for example in the case of a widely used medical object.

Compared to other approaches for registering a navigated structure in a medical navigation system, such as for example performing a 3D scan the object including the object reference, the present registration process is simple and fast once an appropriate adaptor has been identified and provided. In addition, the navigated structure typically has to be registered within a sterilised environment such as an operating theatre. A medical navigation system is usually already present in such an environment, hence only the adaptor and the registration tool have to be sterile when using the approach in accordance with the present invention, whereas the other approach mentioned also requires a sterile scanning apparatus.

In one embodiment, the adaptor comprises a force-generating member which generates a force which pushes the navigated structure and the adaptor towards each other. The force-generating member can be a spring or other elastic element. Pushing the navigated structure and the adaptor towards each other ensures that there is a defined relative position between them. The force can be exerted on the navigated structure or on other parts of the medical object.

In a preferred embodiment, the adaptor parts are designed such that they form the adaptor coupling part in such a manner that it can be connected to the registration tool when the adaptor parts are assembled, preferably only when the adaptor parts are assembled. If the adaptor parts are in a relative position other than the one which defines their assembled state, then the adaptor coupling part cannot be connected to the registration tool coupling part. In one implementation of this embodiment, the assembled adaptor parts constitute the adaptor coupling part which exhibits a predetermined shape, and the registration tool has a recess which exhibits the same predetermined shape. If the adaptor parts are not in their predetermined relative position, then the adaptor coupling part formed by the adaptor parts does not fit into the recess in the registration tool.

In another implementation of this embodiment, the adaptor coupling part comprises a connection-preventing member which prevents a connection between the adaptor coupling part and the registration tool coupling part if the adaptor parts are not properly assembled. The connection-preventing member is for example a blocking member which is retracted when the adaptor parts are properly assembled.

One advantage of this embodiment is that the adaptor parts often cannot be properly assembled if the shape of the navigated structure deviates from its original shape, for example due to damage. This means that a deformed navigated structure cannot be registered and therefore cannot be navigated in the medical navigation system.

There are a number of ways of ensuring that the adaptor parts form the adaptor coupling part in such a manner that it can only be connected to the registration tool when the adaptor parts are assembled. In accordance with one option, at least one adaptor part has a protrusion which engages a recess in another adaptor part when the adaptor parts are assembled. If the protrusion does not engage the recess, there must be a distance between the adaptor parts as compared to their assembled state. If the registration tool comprises a recess for the adaptor coupling part, this means that the adaptor coupling part cannot be inserted into this recess.

In accordance with another option, the adaptor comprises a sleeve which can only be applied to the adaptor if the adaptor parts are assembled. Preferably, the sleeve forms at least part of the adaptor coupling part.

In accordance with another option, the adaptor parts comprise magnets. The effect of the magnets is to hold the adaptor parts together when assembled and/or to generate a repelling force when the adaptor parts are not assembled. It is also possible to combine two or more of these options.

In one embodiment, the structure-receiving recess is at least partly located within the adaptor coupling part. This means that the navigated structure is close to the registration tool during the registration process, which may lead to a more accurate registration result.

In another embodiment, the structure-receiving recess is located away from the adaptor coupling part. This is particularly useful if the working space is constrained, and in particular if the registration tool cannot be arbitrarily positioned.

In one embodiment, the adaptor coupling part is essentially cylindrical. The adaptor coupling part can be a hollow or a solid cylinder. The registration tool coupling part is then a cylindrical recess in the registration tool. Connecting the adaptor to the registration tool would then involve inserting the cylindrical adaptor coupling part into the cylindrical recess in the registration tool. One advantage of the cylindrical shape is that the adaptor coupling part cannot be inserted into the cylindrical recess in the registration tool if the adaptor parts are not assembled. The adaptor coupling part preferably has an alignment member which guarantees a predetermined rotational alignment of the cylindrical adaptor coupling part within the recess in the registration tool. The alignment member can be a radial protrusion of the adaptor coupling part which interacts with a radial extension of the recess in the registration tool.

The present invention also relates to a system comprising an adaptor as described in this document and at least one of a medical object having a navigated structure and a registration tool having a registration tool coupling part for engaging the adaptor coupling part.

It is the function of a marker to be detected by a marker detection device (for example, a camera or an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

It is within the scope of the present invention to combine one or more embodiments and/or options to form a new embodiment wherever this is technically feasible.

Figure 2A:
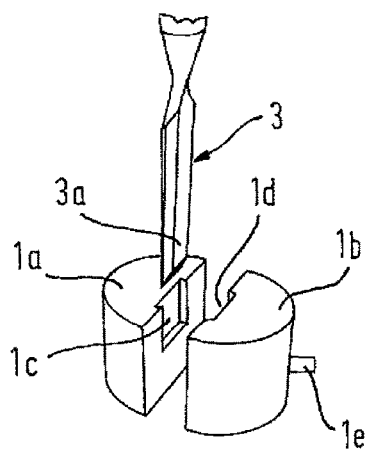
Figure 2B:
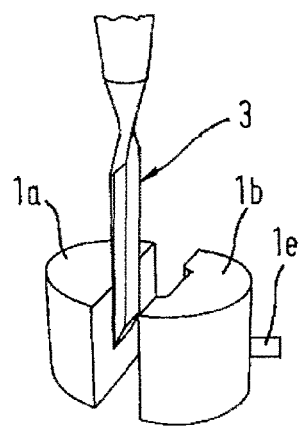
Figure 2C:
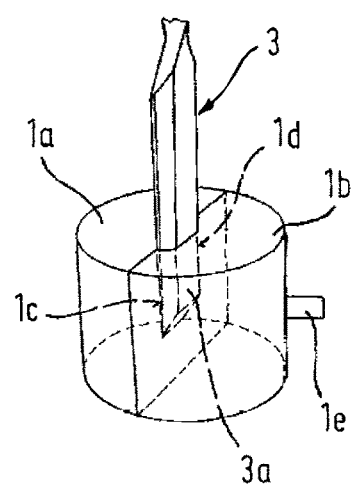
Figure 3:
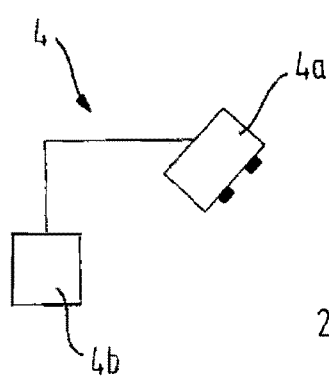

The invention shall now be explained in more detail with reference to the accompanying drawings, which show:

FIG. 1 an adaptor and a registration tool;
FIGS. 2a-c the steps of placing a navigated structure of a medical object in the adaptor;
FIG. 3 an arrangement for registering a navigated structure of the object;
FIGS. 4a-d an adaptor part with a movement prevention member and a force-generating member;
FIG. 5 a first example embodiment of an adaptor;
FIG. 6 a second example embodiment of an adaptor;
FIG. 7 a third example embodiment of an adaptor;
FIG. 8 a fourth example embodiment of an adaptor; and
FIG. 9 a fifth example embodiment of an adaptor.

FIG. 1 shows an adaptor 1 and a registration tool 2. The outer shape of the adaptor 1 resembles two coaxial cylinders which exhibit different diameters and are adjoined in the axial direction. The smaller-diameter cylinder 1g is an example of an adaptor coupling part for connecting the adaptor 1 to the registration tool 2.

The registration tool 2 comprises a body featuring an essentially cylindrical recess 2a which is formed so as to firmly hold the adaptor coupling part 1g. The registration tool 2 also comprises a reference 2b, which in the present example consists of three marker spheres in a known positional relationship. The registration tool 2 can be an Instrument Calibration Matrix (ICM) as sold by the Applicant.

The adaptor 1 can be connected to the registration tool 2 by inserting the adaptor coupling part 1g into the recess 2a in the registration tool, which is an example of a registration tool coupling part. The larger-diameter part of the adaptor 1 acts as a stop which limits the axial movement of the adaptor coupling part 1g into the recess 2a. The adaptor 1 comprises a rotation-preventing member 1e, which in the present example is a radial pin extending outwards from the surface of the adaptor coupling part 1g. The recess 2a in the registration tool 2 comprises a corresponding radial extension in order to accommodate the pin 1e. The interaction between the pin 1e and the radial extension of the recess 2a prevents a rotational movement between the adaptor 1 and the registration tool 2. If the step between the two cylindrical parts of the adaptor 1 abuts the surface of the registration tool 2, and the pin 1e interacts with the radial extension of the recess 2a, then there is a known relative position between the adaptor 1 and the registration tool 2.

FIGS. 2a to 2c show the steps of placing a medical object, which in the present example is a chisel, in the adaptor 1. For the sake of simplicity, FIGS. 2a to 2c only show the smaller-diameter part of the adaptor 1, i.e. the adaptor coupling part 1g.

The adaptor 1 comprises two adaptor parts 1a and 1b. The adaptor part 1a comprises a recess 1c, and the adaptor part 1b comprises a recess 1d. When the adaptor parts are assembled, the recesses 1c and 1d in the adaptor parts 1a and 1b form a structure-receiving recess in the shape of a navigated structure, which in the present example is the distal portion of a chisel 3. In the state shown in FIG. 2a, the adaptor parts 1a and 1b are separated and the navigated structure 3a is located outside the structure-receiving recess.

In the state shown in FIG. 2b, the navigated structure is partly located within the recess 1c in the adaptor part 1a and partly projects from the surface of the adaptor part 1a. FIG. 2c shows the adaptor parts 1a and 1b in their assembled state. The navigated structure 3a completely fills the structure-receiving recess formed by the recesses 1c and 1d. In the state shown in FIG. 2c, the navigated structure 3a is in a known position relative to the adaptor 1. The navigated structure 3a of the chisel 3 shown by way of example in FIGS. 2a to 2c could also be inserted into the structure-receiving recess after the adaptor parts 1a and 1b have been assembled. If the navigated structure 3a has a different shape, however, in particular a non-linear shape, then the approach of having at least two adaptor parts which can be separated in order to insert the navigated structure 3a has the advantage of allowing navigated structures of any shape to be placed in the correspondingly shaped structure-receiving recess of the adaptor 1. The number of adaptor parts and the shape of the recesses in the respective parts depend solely on the shape of the navigated structure.

Once the navigated structure 3a is completely located in the structure-receiving recess of the adaptor 1, the adaptor 1 and the registration tool 2 are connected in a predetermined relative position. In the present case, the adaptor coupling part 1g is inserted into the recess 2a until the shoulder of the adaptor 1 abuts the surface of the registration tool 2.

This is schematically shown in FIG. 3. As can be seen in this figure, the medical object 3 carries a reference 3b, which in the present example is a marker device comprising three marker spheres in a known positional relationship.

FIG. 3 also shows a medical navigation system 4 comprising a stereoscopic camera 4a and a control unit 4b. The control unit 4b comprises a memory for storing and/or an interface for accessing a database which comprises the shape of the adaptor 1 and registration tool 2. The shape of the adaptor 1 means at least the positional relationship between the adaptor coupling part 1g and the structure-receiving recess. The shape of the registration tool 2 means at least the positional relationship between the reference 2b and the registration tool coupling part 2a.

The camera 4a captures a stereoscopic image of the adaptor 1, the registration tool 2 and the chisel 3. The medical navigation system 4 determines the relative position between the registration tool reference 2b and the medical object reference 3b. This relative position must equal the sum of: the relative position between the registration tool reference 2b and the registration tool coupling part 2a; the relative position between the adaptor coupling part 1g and the structure-receiving recess; and the relative position between the navigated structure 3a and the object reference 3b. Since the first two relative positions are known, the relative position between the navigated structure 3a and the object reference 3b can be calculated, i.e. the navigated structure 3a can be registered in the medical navigation system 4.

This registration requires the navigated structure 3a and the adaptor 1, in particular the adaptor coupling part 1g, to be in a known positional relationship. This can be guaranteed by a movement prevention member which prevents a relative movement between the navigated structure 3a and the adaptor 1 when the adaptor parts 1a and 1b are assembled and the navigated structure 3a is located in the structure-receiving recess. In many cases, the shape of the navigated structure 3a, and therefore correspondingly the shape of the structure-receiving recess, generate a form-fit lock which prevents the relative movement. The movement prevention member is then part of the surface of at least one adaptor part which constitutes the structure-receiving recess.

Figure 4A:
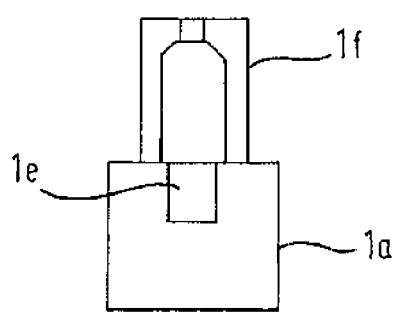
Figure 4B:
Figure 4C:
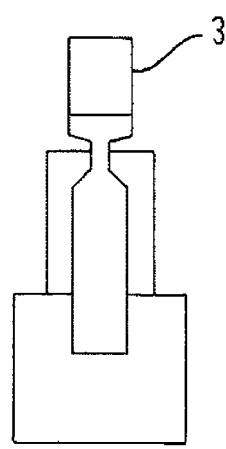

The navigated structure 3a of the chisel 3 is such that the medical object could be removed from the adaptor 1 when the adaptor parts 1a and 1b are assembled. In order to prevent this, the adaptor 1 optionally comprises a dedicated movement prevention member 1f as shown in FIGS. 4a to 4d. FIG. 4a shows a top view of an adaptor part 1a comprising the movement prevention member 1f. The movement prevention member if is basically an extension which forms a collar for a part of the chisel 3. As can be seen in the side view in FIG. 4b, the movement prevention member 1f comprises a cavity which holds a part of the chisel 3, as shown in FIG. 4c. The chisel 3 comprises a constriction between its handle and its blade. When this constriction is located in the cavity of the movement prevention member 1f, the navigated structure 3a is securely held within the structure-receiving recess of the adaptor 1.

Figure 4D:
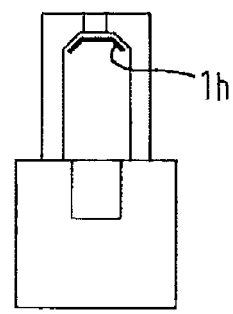

As shown in FIG. 4d, the adaptor part 1a can also comprise a force-generating member 1h which generates a force which pushes the navigated structure 3a and the adaptor 1 towards each other. The force-generating member 1h is for example a spring-loaded pusher. If the blade of the chisel 3 in the present example is shorter than the length for which the adaptor 1 was produced, then the force-generating member 1h pushes the chisel 3 towards the adaptor 1 until the navigated structure 3a abuts the bottom of the structure-receiving recess, such that the navigated structure 3a is in a known position relative to the adaptor 1.

FIG. 5 shows a first specific example embodiment of an adaptor 5 comprising adaptor parts 5a and 5b which, when assembled as shown in the right-hand portion of FIG. 5, constitute the structure-receiving recess for the medical object 3. When assembled, the adaptor parts 5a and 5b exhibit an outer shape comprising three adjoining coaxial cylinders of increasing diameter. The adaptor 5 can optionally comprise a rotation-preventing member similar to the pin 1e of the adaptor 1, for example on the medium-diameter cylinder. The adaptor 5 also comprises a ring-like sleeve 5c, wherein the inner diameter of the sleeve 5c is equal to the outer diameter of the smallest-diameter cylinder of the adaptor parts 5a and 5b, and the outer diameter of the sleeve 5c is equal to the outer diameter of the medium-diameter cylinder of the adaptor parts 5a and 5b.

Given this design, the sleeve 5c can only be slid onto the smallest-diameter cylinder of the adaptor parts 5a and 5b if they are assembled. Otherwise, there is a gap between the adaptor parts 5a and 5b which prevents the sleeve 5c from being assembled. When the sleeve 5c is attached, the sleeve 5c and the medium-diameter cylinder formed by the adaptor parts 5a and 5b constitute the adaptor coupling part.

FIG. 6 shows another adaptor 6 in a second specific example embodiment. One adaptor part 6a comprises a recess 6c and at least one hole 6f—in the present example, four holes. A second adaptor part 6b comprises a corresponding number of pins 6e, i.e. four pins in the present example, and a recess 6d. When the adaptor parts 6a and 6b are assembled, the recesses 6c and 6d constitute the structure-receiving recess. The adaptor parts 6a and 6b can only be assembled when the pins 6e engage the holes 6f, which establishes a predetermined relative position between the adaptor parts 6a and 6b.

FIG. 7 shows another adaptor 7 in a third specific example embodiment. The first adaptor part 7a comprises magnets 7c and 7d, and the second adaptor part 7b comprises magnets 7e and 7f. When the adaptor parts 7a and 7b are assembled, the magnet 7c interacts with the magnet 7f while the magnet 7d interacts with the magnet 7e. The pole of the magnet 7d which faces the magnet 7e is preferably the opposite of the pole of the magnet 7c which faces the magnet 7f. Given this configuration, the magnets not only hold the adaptor parts 7a and 7b firmly together when assembled but also actively prevent them from being assembled in an incorrect relative position.

FIG. 8 shows another adaptor 8 in a fourth specific example embodiment. A first adaptor part 8a comprises a protrusion 8c which exhibits a particular shape—in the present example, a dovetail shape. The adaptor part 8b comprises a recess 8d which exhibits the same shape as the protrusion 8c. This combination of the protrusion 8c and the recess 8d ensures that there is only one relative orientation between the adaptor parts 8a and 8b in which they can be properly assembled.

FIG. 9 shows another adaptor 9 in a fifth specific example embodiment. While the structure-receiving recess of the adaptors 5, 6, 7 and 8 at least partly extends into the adaptor coupling part, the structure-receiving recess of the adaptor 9 is located away from the adaptor coupling part 9c. This allows the navigated structure 3a to be registered even when the working space available for positioning the registration tool 2 and the medical object 3 is limited. The shape and size of the part of the adaptor 9 between the structure-receiving recess and the adaptor coupling part 9c can be freely selected, depending on workspace constraints.

It is possible to combine features of at least two of the adaptors 5, 6, 7, 8 and 9.

In order to manufacture an adaptor, the shape of the navigated structure has to be known. The shape can for example be derived from a three-dimensional dataset used for manufacturing the medical object or by scanning the medical object, for example using stereoscopic imaging or laser scanning. The adaptor can be mass-produced, in particular if the medical object in question is widely used. Another option is to manufacture the adaptor by rapid prototyping, for example using laser sintering. The adaptor can in particular be manufactured within a sterile environment.

The invention claimed is:

1. An adaptor configured to receive a navigated structure, the navigated structure being at least part of a medical object that carries an object reference, and the adaptor further configured to be connected to a registration tool in order to register the navigated structure in a medical navigation system, the adaptor comprising:
at least two adaptor parts configured such that, only on condition that the at least two adaptor parts are assembled to form an assembly with a predetermined relative position between each of the at least two adaptor parts, the assembly of the at least two adaptor parts forms:
a structure-receiving recess in the shape of the navigated structure, and
an adaptor coupling part configured to connect the adaptor to the registration tool in a predetermined relative position, the adaptor coupling part having a predetermined shape that is the same as the shape of a coupling recess of the registration tool.

2. The adaptor according to claim 1, further comprising a movement prevention member that prevents a relative movement between the navigated structure and the adaptor in the condition that the adaptor parts are assembled and the navigated structure is located in the structure-receiving recess.

3. The adaptor according to claim 1, further comprising a force-generating member that generates a force that pushes the navigated structure and the adaptor towards each other.

4. The adaptor according to claim 1, wherein at least one adaptor part of the at least two adaptor parts has a protrusion that engages a recess in another adaptor part of the at least two adaptor parts in the condition that the at least two adaptor parts are assembled.

5. The adaptor according to claim 1, comprising a sleeve that can only be applied to the adaptor in the condition that the at least two adaptor parts are assembled.

6. The adaptor according to claim 5, wherein the sleeve forms at least part of the adaptor coupling part.

7. The adaptor according to claim 1, wherein the at least two adaptor parts comprise magnets.

8. The adaptor according to claim 1, wherein the structure-receiving recess is at least partly located within the adaptor coupling part.

9. The adaptor according to claim 1, wherein the structure-receiving recess is located away from the adaptor coupling part.

10. The adaptor according to claim 1, wherein the adaptor coupling part is a cylinder.

11. A system comprising:
a medical object having a navigated structure;
a registration tool having a registration tool coupling part for engaging an adaptor coupling part; and
an adaptor configured to receive the navigated structure, and to be engaged to the registration tool coupling part of the registration tool in order to register the navigated structure in a medical navigation system, the adaptor comprising:
at least two adaptor parts configured such that, only on condition that the at least two adaptor parts are assembled to form an assembly with a predetermined relative position between each of the at least two adaptor parts, the assembly of the at least two adaptor parts forms:
a structure-receiving recess in the shape of the navigated structure, and
the adaptor coupling part configured to connect the adaptor to the registration coupling part of the registration tool in a predetermined relative position, the adaptor coupling part having a predetermined shape that is the same as the shape of a coupling recess of the registration tool coupling part.

12. A method of registering a navigated structure, wherein the navigated structure is at least part of a medical object that carries an object reference, in a medical navigation system, the method comprising:
providing an adaptor configured to receive the navigated structure and to connect to a registration tool in order to register the navigated structure in the medical navigation system, the adaptor comprising at least two adaptor parts;
assembling the at least two adaptor parts to form an assembly with a predetermined relative position between each of the at least two adaptor parts, the assembly of the at least two adaptor parts forming:
a structure-receiving recess in the shape of the navigated structure with the navigated structure being located within the structure-receiving recess; and
an adaptor coupling part configured to connect the adaptor to the registration tool in a predetermined relative position, the adaptor coupling part having a predetermined shape that is the same as the shape of a coupling recess of the registration tool,
wherein the structure-receiving recess and the adaptor coupling part are only formed on condition that the at least two adaptor parts are assembled into the assembly;
coupling the adaptor coupling part to a registration tool coupling part of the registration tool, the registration tool coupling part comprising the coupling recess, and a registration tool reference;
determining a relative reference position between the object reference and the registration tool reference; and
registering the navigated structure by calculating a relative position between the navigated structure and the object reference from the determined relative reference position between the object reference and the registration tool reference, a known relative position between the registration tool reference and the registration tool coupling part, and a known relative position between the adaptor coupling part and the structure-receiving recess.

* * * * *